US012746217B2

(12) United States Patent
Balcombe et al.

(10) Patent No.: US 12,746,217 B2
(45) **Date of Patent: *Sep. 29, 2026**

(54) METHOD OF INHIBITING DOPAMINE TRANSPORTER ACTIVITY

(71) Applicant: SpecNova LLC, Evergreen, CO (US)

(72) Inventors: Sebastian Balcombe, Evergreen, CO (US); William Hamilton, Cambridge (GB); Jonathan Heal, Cambridge (GB); Joseph Sheridan, Cambridge (GB)

(73) Assignee: SPECNOVA LLC, Tysons Corner, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/912,005

(22) Filed: Oct. 10, 2024

(65) Prior Publication Data

US 2025/0032426 A1 Jan. 30, 2025

Related U.S. Application Data

(62) Division of application No. 17/655,020, filed on Mar. 16, 2022, now abandoned.

(60) Provisional application No. 63/162,347, filed on Mar. 17, 2021.

(51) Int. Cl.

| | |
|---|---|
| ***A61K 31/05*** | (2006.01) |
| ***A61K 31/352*** | (2006.01) |
| ***A61K 31/353*** | (2006.01) |
| ***A61K 45/06*** | (2006.01) |

(52) U.S. Cl.

CPC ............ *A61K 31/05* (2013.01); *A61K 31/352* (2013.01); *A61K 31/353* (2013.01); *A61K 45/06* (2013.01)

(58) Field of Classification Search

CPC ...... A61K 31/05; A61K 31/353; A61K 45/06; A61K 31/352; A61P 25/16; A61P 25/30

See application file for complete search history.

(56) References Cited

U.S. PATENT DOCUMENTS

| | | | | |
|---|---|---|---|---|
| 11,986,457 | B2 * | 5/2024 | Balcombe .............. | A61K 45/06 |
| 2006/0177409 | A1 | 8/2006 | Arnaud | |
| 2022/0296537 | A1 | 9/2022 | Balcombe et al. | |

FOREIGN PATENT DOCUMENTS

| | | | | |
|---|---|---|---|---|
| KR | 20110133277 A | * 12/2011 | .............. | A61P 19/10 |

OTHER PUBLICATIONS

Tripp G, Wickens JR. Neurobiology of ADHD. Neuropharmacology. Dec. 2009;57(7-8):579-89 (Year: 2009).*
www.thebiotek.com/product/bt-1443289 (downloaded Oct. 11, 2023). (Year: 2023).*
Balogh, B.; Anderson, A. B. Phytochemistry 1965, 4, 569-575. (Year: 1965).*
Ryu Jae Ha KR20110133277A—machine English translation. (Year: 2011).*
Russell, et al., Neurotherapeutics. Jul. 2019;16(3):649-665. (Year: 2019).*
Zhang, Y.-M., et al., (2005), Chemistry & Biodiversity, 2: 497-505 (Year: 2005) (Year: 2005).*
Lovell, P., Kasimi, B., Carleton, J. et al. Living without DAT: Loss and compensation of the dopamine transporter gene in sauropsids (birds and reptiles). Sci Rep 5, 14093 (2015). https://doi.org/10.1038/srep14093. (Year: 2015).*
Li XN, Chu C, Cheng DP, Tong SQ, Yan JZ. Norlignans from Asparagus cochinchinensis. Nat Prod Commun. Oct. 2012;7(10):1357-8. PMID: 23157009 (Year: 2012).*
Agataresinol Relif, yami.com, printed Dec. 11, 2025 (Year: 2025).*
Jung, K. H., Choi, H. L., Park, S., Lee, G., Kim, M., Min, J. K., et al. (2014). The effects of the standardized herbal formula PM014 on pulmonary inflammation and airway responsiveness in a murine model of cockroach allergen-induced asthma. J. Ethnopharmacol. 155 (1), 113-122, 2014. (Year: 2014).*
Wang M, Wang S, Hu W, Wang Z, Yang B and Kuang H (2022), Asparagus cochinchinensis: A review of its botany, traditional uses, phytochemistry, doi: 10.3389/fphar.2022.1068858. (Year: 2022).*
Frezza C, et al., Molecules. Jan. 3, 2020;25(1):197. (Year: 2020).*
Agatharesinol, V.; Enzell, C. R.; Thomas, B.R. Tetrahedron Letters (1966), (22), 2395-402.
Chen XH, Kim CS, Kashiwagi T, Tebayashi S, Horiike M. Antifeedants against Acusta despesta from the Japanese cedar, Cryptomeria japonica. Z Naturforsch CJ Biosci. Mar.-Apr. 2001;56(3-4):249-52. doi: 10.1515/znc-2001-3-413. PMID: 11371016. ( Year: 2001).
Davies, N.T., Wu, HF. & Altaner, C.M. The chemistry and bioactivity of various heartwood extracts from redwood (*Sequoia sempervirens*) against two species of fungi. N.Z. j. of For. Sci. 44, 17 (2014). https://doi.org/10.1186/s40490-014-0017-4.
Zhang, Y.-M., et al., (2005), Chemistry & Biodiversity, 2: 497-505 (Year: 2005).
Liao-Bin Dong, Juan He, Yuan-Yuan Wang, Xing-De Wu, Xu Deng, Zheng-Hong Pan, Gang Xu, Li-Yan Peng, Yu Zhao, Yan Li, Xun Gong, and Qin-Shi Zhao Journal of Natural Products 2011 7 4 (2), 234-239 DOI: 10.1021/np100694k.

(Continued)

*Primary Examiner* — Clinton A Brooks
*Assistant Examiner* — Izabela Schmidt
(74) *Attorney, Agent, or Firm* — HESLIN ROTHENBERG FARLEY & MESITI P.C.

(57) ABSTRACT

The invention relates to pharmaceutical compositions comprising dopamine transporter inhibitors and to their use in the prophylaxis or treatment of disease states or conditions mediated by the dopamine transporter.

14 Claims, No Drawings

(56) References Cited

OTHER PUBLICATIONS

C.R. Enzell, Y. Hirose, B. R. Thomas, The chemistry of the order araucariales 6. Absolute configurations of agatharesinol hinokiresinol and sugiresinol, Agatharesinol, V.; Enzell, C. R.; Thomas, B. R. Tetrahedron Letters (1967), (9), 793-798.
Balogh, B.; Anderson, A B. Phytochemistry 1965, 4, 569-575.
Enzell, C. R.; Thomas, B. R. Tetrahedron Letters (1967), (9), 793-798.
Hatam et al., J. Chem. Soc. C, 1969, 1921-1932 https://pubs.rsc.org/en/contenUarticlehtml/1969/j3/j39690001921.
https://dailymed.nlm.nih.gov/dailymed/drugInfo.cfm?setid=eaebea7a-d02c-5673-e053-2995a90a581e (Year: 2024).
Zhang, Y.-M., Tan, N.-H., Yang, Y.-B., Lu, Y., Cao, P. and Wu, Y.-S. (2005), Norlignans from Sequoia sempervirens. Chemistry & Biodiversity, 2: 497-505. (Year: 2005).
Agatharesinol acetonide https://www.thebiotek.com/product/bt-1443289 (Year: 2023).

* cited by examiner

METHOD OF INHIBITING DOPAMINE TRANSPORTER ACTIVITY

CROSS REFERENCE TO RELATED APPLICATIONS

This application is a divisional of U.S. application Ser. No. 17/655,020, filed on Mar. 16, 2022, which claims priority to U.S. provisional application No. 63/162,347, filed on Mar. 17, 2021. The entire contents of each of the earlier applications are hereby incorporated herein by reference.

FIELD OF THE INVENTION

The invention relates to pharmaceutical compositions comprising dopamine transporter inhibitors and to their use in the prophylaxis or treatment of disease states or conditions mediated by the dopamine transporter.

BACKGROUND OF THE INVENTION

The dopamine transporter (also known as the dopamine active transporter, DAT, SLC6A3) is a membrane-spanning protein that pumps the neurotransmitter dopamine out of the synaptic cleft back into cytosol. In the cytosol, other transporters sequester the dopamine into vesicles for storage and later release. Dopamine reuptake via DAT provides the primary mechanism through which dopamine is cleared from synapses, although there may be an exception in the prefrontal cortex, where evidence points to a possibly larger role of the norepinephrine transporter.

The gene that encodes the DAT protein is located on human chromosome 5, consists of 15 coding exons, and is roughly 64 kbp long. Evidence for the associations between DAT and dopamine related disorders has come from a type of genetic polymorphism, known as a VNTR, in the DAT gene (DAT1), which influences the amount of protein expressed.

DAT is implicated in a number of dopamine-related disorders, therefore, there is a need to provide effective dopamine transporter inhibitors.

SUMMARY OF THE INVENTION

According to a first aspect of the invention, there is provided a pharmaceutical composition comprising a compound selected from: agatharesinol or a pharmaceutically acceptable derivative thereof; or kazinol U; or a pharmaceutically acceptable salt or solvate thereof.

DETAILED DESCRIPTION OF THE INVENTION

Dopamine Transporter Inhibitors

According to a first aspect of the invention, there is provided a pharmaceutical composition comprising a compound selected from: agatharesinol or a pharmaceutically acceptable derivative thereof; or kazinol U; or a pharmaceutically acceptable salt or solvate thereof.

In one embodiment, the compound is agatharesinol, or a pharmaceutically acceptable salt or solvate thereof.

References herein to "agatharesinol" refer to a compound having the following structure:

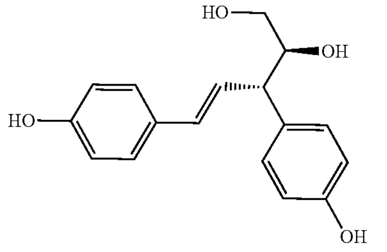 [SMILES: OC[C@@H](O)[C@@H](/C=C/c1ccc(O)cc1)c1ccc(O)cc1]

Agatharesinol (MolPort Number 039-141-773; CAS Number 7288-11-1; PubChem CID 15558522) is known chemically as (2S,3S,4E)-3,5-bis(4-hydroxyphenyl)pent-4-ene-1,2-diol. Agatharesinol is a naturally occurring compound which has been previously characterised as a major heartwood norlignane, however, this compound has neither previously been formulated in a pharmaceutical composition nor disclosed for being of potential use in the treatment of a disease state or condition mediated by the dopamine transporter. Data is provided herein which shows that agatharesinol demonstrated an extremely high level of inhibition in the dopamine transporter inhibitory assay.

In one embodiment, the compound is agatharesinol, or a pharmaceutically acceptable derivative thereof, or a pharmaceutically acceptable salt or solvate thereof.

References herein to a "pharmaceutically acceptable derivative of agatharesinol" refer to any compound which, upon administration to the recipient, is capable of providing (directly or indirectly) agatharesinol or an active metabolite or residue thereof. In one embodiment, the pharmaceutically acceptable derivative of agatharesinol is sequirin C.

References herein to "sequirin C" refer to a compound having the following structure:

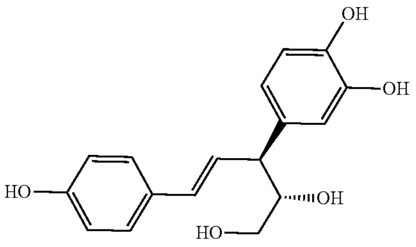 [SMILES: OC[C@@H](O)[C@@H](/C=C/c1ccc(O)cc1)c1ccc(O)c(O)c1]

Sequirin C (MolPort Number 039-338-294; CAS Number 18194-29-1; PubChem CID 12315463) is known chemically as 4-[(1S,2E)-1-[(1S)-1,2-dihydroxyethyl]-3-(4-hydroxyphenyl)prop-2-en-1-yl]benzene-1,2-diol. Sequirin C is a naturally occurring compound which has been previously characterised as a norlignan that is a derivative of agatharesinol in which the second aromatic ring has an additional hydroxy substituent ortho to the one present in the parent compound. It is believed to have a role as a metabolite, however, this compound has neither previously been formulated in a pharmaceutical composition nor disclosed for being of potential use in the treatment of a disease state or condition mediated by the dopamine transporter. Data is provided herein which shows that sequirin C demonstrated an extremely high level of inhibition in the dopamine transporter inhibitory assay.

According to a further aspect of the invention, there is provided a pharmaceutical composition comprising a compound selected from: agatharesinol; or sequirin C; or kazinol U; or a pharmaceutically acceptable salt or solvate thereof.

According to a further aspect of the invention, there is provided a pharmaceutical composition comprising a compound selected from: agatharesinol; or sequirin C; or a pharmaceutically acceptable salt or solvate thereof.

In one embodiment, the compound is kazinol U, or a pharmaceutically acceptable salt or solvate thereof.

References herein to "kazinol U" refer to a compound having the following structure:

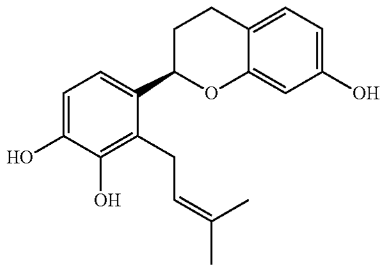 [SMILES: CC(C)=CCc1c([C@H]2CCc3ccc(O)cc3O2)ccc(O)c1O]

Kazinol U (MolPort Number 039-337-109; CAS Number 1238116-48-7; PubChem CID 51136520) is known chemically as 4-[(2S)-7-hydroxy-3,4-dihydro-2H-chromen-2-yl]-3-(3-methylbut-2-enyl)benzene-1,2-diol. Kazinol U is a naturally occurring compound which has been previously characterised as a prenylated flavan isolated from *Broussonetia kazinoki*, however, this compound has neither previously been formulated in a pharmaceutical composition nor disclosed for being of potential use in the treatment of a disease state or condition mediated by the dopamine transporter. Data is provided herein which shows that kazinol U demonstrated a high level of inhibition in the dopamine transporter inhibitory assay.

References to compounds of the invention also include ionic forms, salts, solvates, isomers (including geometric and stereochemical isomers), tautomers, esters, prodrugs, isotopes and protected forms thereof, for example, as discussed below; preferably, the salts or tautomers or isomers or solvates thereof; and more preferably, the salts or tautomers or solvates thereof, even more preferably the salts or tautomers or solvates thereof. Hereinafter, compounds and their ionic forms, salts, solvates, isomers (including geometric and stereochemical isomers), tautomers, esters, prodrugs, isotopes and protected forms thereof as defined in any aspect of the invention (except intermediate compounds in chemical processes) are referred to as "compounds of the invention".

Salts

Certain compounds of the invention can exist in the form of salts, for example acid addition salts or, in certain cases salts of organic and inorganic bases such as carboxylate, sulfonate and phosphate salts. All such salts are within the scope of this invention, and references to compounds of the invention include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (+)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

The compounds of the invention may exist as mono- or di-salts depending upon the $pK_a$ of the acid from which the salt is formed.

It will be appreciated that for use in medicine the salts of the compounds of the invention should be pharmaceutically acceptable. Suitable pharmaceutically acceptable salts will be apparent to those skilled in the art. Pharmaceutically acceptable salts include those described by Berge, Bighley and Monkhouse, *J. Pharm. Sci.* 1977, 66, pp. 1-19. Such pharmaceutically acceptable salts include acid addition salts formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates may be used, for example in the isolation of compounds of the invention and are included within the scope of this invention. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Certain of the compounds of the invention may form acid addition salts with one or more equivalents of the acid. The present invention includes within its scope all possible stoichiometric and non-stoichiometric forms.

Solvates

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compounds of the invention are within the scope of the invention. In one embodiment, the pharmaceutically acceptable solvates of the compounds of the invention include the hydrate thereof.

Prodrugs

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in *Drugs of Today,* 19, 9, 1983, 499-538 and in *Topics in Chemistry, Chapter* 31, pp. 306-316 and in "*Design of Prodrugs*" by H. Bundgaard, Elsevier, 1985, Chapter 1. It will further be appreciated by those skilled in the art, that certain moieties, known to those skilled in the art as "pro-moieties", for example as described by H. Bundgaard in "*Design of Prodrugs*" may be placed on appropriate functionalities when such functionalities are present within compounds of the invention.

Certain specific examples of pro-drugs include sulphonated, glucuronidated, methylated, esterificated, acetylated, glutathionated and glycine conjugated derivatives of the compounds of the invention.

Also included within the scope of the compounds and various salts of the invention are polymorphs thereof.

Enantiomers

Where chiral centres are present in compounds of the invention, the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

Isotopes

The subject invention also includes all pharmaceutically acceptable isotopically-labelled compounds which are identical to those recited in the compounds of the invention but for the fact that one or more atoms are replaced by an atom having an atomic mass or mass number different from the atomic mass or mass number most commonly found in nature.

Examples of isotopes suitable for inclusion in the compounds of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of the invention, for example, those incorporating a radioactive isotope, are useful in drug and/or substrate tissue distribution studies. The compounds of the invention can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase) etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^{2}H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labelled compounds of the invention can generally be prepared by conventional techniques known to those skilled in the art using appropriate isotopically-labelled reagents in place of the non-labelled reagent previously employed.

Purity

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the pharmaceutical compositions.

Processes

It will be apparent that the claimed compounds of the invention are known compounds and may either be purchased commercially or may be prepared in accordance with known procedures.

Pharmaceutical Compositions

In one embodiment the pharmaceutical composition is a sterile pharmaceutical composition.

The present invention further provides pharmaceutical compositions, as defined above, and methods of making a pharmaceutical composition comprising (e.g. admixing) at least one compound of the invention, together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one particular embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another particular embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compounds of the invention may be formulated with a carrier and administered in the form of nanoparticles, the increased surface area of the nanoparticles assisting their absorption. In addition, nanoparticles offer the possibility of direct penetration into the cell.

Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Particularly, the compositions comprise from approximately 20% (w/w) to approximately 90%, % (w/w) active ingredient and from 80% (w/w) to 10% of a pharmaceutically acceptable excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g. solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Therapeutic Utility

According to a further aspect of the invention, there is provided the pharmaceutical composition as defined herein, for use in therapy.

Furthermore, the compounds of the invention are inhibitors of dopamine transporter activity, and which may be useful in preventing or treating disease states or conditions mediated by the dopamine transporter. Thus, according to a further aspect of the invention there is provided the pharmaceutical composition as defined herein, for use in the prophylaxis or treatment of a disease state or condition mediated by the dopamine transporter.

Examples of disease states or conditions mediated by the dopamine transporter include: Parkinson's disease, bipolar disorder, clinical depression, attention deficit hyperactivity disorder (ADHD), narcolepsy, obstructive sleep apnea, night shift disorders, mood disorders, obesity, appetite suppression, cocaine addiction, methamphetamine addiction, antidepressant addiction, alcohol addiction and smoking addiction.

The compounds of the present invention may be useful for the treatment of the adult population. The compounds of the present invention may be useful for the treatment of the pediatric population.

Methods of Treatment

According to a further aspect of the invention there is provided a method of treating a disease state or condition mediated by the dopamine transporter which comprises administering to a subject in need thereof the pharmaceutical composition as described herein. Examples of such disease states and conditions are set out above.

The compounds are generally administered to a subject in need of such administration, for example a human or animal patient, particularly a human.

The compounds will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required.

The compound of the invention can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

In another particular dosing schedule, a patient is given the compound orally once a week.

In another particular dosing schedule, a patient is given the compound orally once-daily for between 7 and 28 days such as 7, 14 or 28 days.

In another particular dosing schedule, a patient is given the compound orally once-daily for 1 day, 2 days, 3 days, 5 days or 1 week followed by the required amount of days off to complete a one or two week cycle.

In another particular dosing schedule, a patient is given the compound orally once-daily for 2 weeks followed by 2 weeks off.

In another particular dosing schedule, a patient is given the compound orally once-daily for 2 weeks followed by 1 week off.

In another particular dosing schedule, a patient is given the compound orally once-daily for 1 week followed by 1 week off.

Ultimately, however, the quantity of compound administered and the type of composition used will be commensurate with the nature of the disease or physiological condition being treated and will be at the discretion of the physician.

It will be appreciated that DAT inhibitors can be used as a single agent or in combination with other DAT inhibitors. Combination experiments can be performed, for example, as described in Chou T C, Talalay P. Quantitative analysis of dose-effect relationships: the combined effects of multiple drugs or enzyme inhibitors. Adv Enzyme Regulat 1984; 22:27-55.

The compounds as defined herein can be administered as the sole therapeutic agent or they can be administered in combination therapy with one of more other compounds (or therapies) for treatment of a particular disease state or condition. For the treatment of the above conditions, the compounds of the invention may be advantageously employed in combination with one or more other medicinal agents, more particularly, other DAT inhibitors or therapeutic agents specific for the disorder being treated.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compounds of the invention may be using in combination with one or more other agents which are administered according to their existing combination regimen. Examples of standard combination regimens are provided below.

Where the compound of the invention is administered in combination therapy with one, two, three, four or more other therapeutic agents (particularly one or two, more particularly one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

In one embodiment is provided a compound of the invention for the manufacture of a medicament for use in therapy wherein said compound is used in combination with one, two, three, or four other therapeutic agents. In another embodiment is provided a medicament for treating a disease state or condition mediated by dopamine transporter inhibition which comprises a compound of the invention wherein said medicament is used in combination with one, two, three, or four other therapeutic agents.

It will be appreciated that the particular method and order of administration and the respective dosage amounts and regimes for each component of the combination will depend on the particular other medicinal agent and compound of the present invention being administered, their route of administration, the particular disease being treated and the particular host being treated. The optimum method and order of administration and the dosage amounts and regime can be readily determined by those skilled in the art using conventional methods and in view of the information set out herein.

The weight ratio of the compound according to the present invention and the one or more other therapeutic agent(s) when given as a combination may be determined by the person skilled in the art. Said ratio and the exact dosage and frequency of administration depends on the particular compound according to the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the present invention. A particular weight ratio for the present compound of the invention and another therapeutic agent may range from 1/10 to 10/1, more in particular from 1/5 to 5/1, even more in particular from 1/3 to 3/1.

For use in combination therapy with another therapeutic agent, the compound of the invention and one, two, three, four or more other therapeutic agents can be, for example, formulated together in a dosage form containing two, three, four or more therapeutic agents i.e. in a unitary pharmaceutical composition containing all agents. In an alternative embodiment, the individual therapeutic agents may be formulated separately and presented together in the form of a kit, optionally with instructions for their use.

In one embodiment is provided a combination of a compound of the invention with one or more (e.g. 1 or 2) other therapeutic agents.

In another embodiment is provided a compound of the invention in combination with one or more (e.g. 1 or 2) other therapeutic agents for use in therapy, such as in the prophylaxis or treatment of a disease state or condition mediated by dopamine transporter inhibition.

In one embodiment the pharmaceutical composition comprises a compound of the invention together with a pharmaceutically acceptable carrier and optionally one or more therapeutic agent(s).

In another embodiment the invention relates to the use of a combination according to the invention in the manufacture of a pharmaceutical composition for inhibiting the dopamine transporter.

In a further embodiment the invention relates to a product containing a compound of the invention and one or more therapeutic agent, as a combined preparation for simultaneous, separate or sequential use in the treatment of patients suffering from a disease state or condition mediated by dopamine transporter inhibition.

BIOLOGICAL DATA

Human Dopamine Transporter (DAT) Binding (Antagonist Radioligand) Assay

Cell membrane homogenates (20 µg protein) are incubated for 120 min at 4° C. with 4 nM of radiolabelled derivative of the high-affinity dopamine (DA) uptake inhibitor 1-[1-(2-benzo [b] thienyl)cyclohexyl]piperidine [$^3$H] BTCP in the absence or presence of the test compound in a buffer containing 50 mM Tris-HCl (pH 7.4) and 100 mM NaCl. Nonspecific binding is determined in the presence of 10 µM BTCP. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is BTCP, which is tested in each experiment at several concentrations to obtain a competition curve from which its $IC_{50}$ is calculated (Pristupa et al (1994) Mol. Pharmacol. 45, 125).

The compounds of the invention were tested in the above mentioned assay which and the results are shown in the following table:

| Compound | % Inhibition of Control Specific Binding | % of Control Specific Binding (1$^{st}$ Test) | % of Control Specific Binding (2$^{nd}$ Test) | % of Control Specific Binding (mean of two tests) |
|---|---|---|---|---|
| Agatharesinol | 95 | 4.2 | 5 | 4.6 |
| Sequirin C | 94 | 7.4 | 5.6 | 6.5 |
| Kazinol U | 62 | 33.6 | 42.8 | 38.2 |

The invention claimed is:

1. A method of treating a disease state or condition mediated by the dopamine transporter, said method comprising administering to a subject in need thereof a dopamine transporter activity (DAT) inhibiting pharmaceutical composition comprising a compound selected from: agatharesinol, sequirin C, and kazinol U, or a pharmaceutically acceptable salt or solvate thereof.

2. The method according to claim 1, wherein the compound is agatharesinol or a pharmaceutically acceptable salt or solvate thereof.

3. The method according to claim 1, wherein the compound is agatharesinol or a pharmaceutically acceptable salt thereof.

4. The method according to claim 1, wherein the compound is sequirin C or a pharmaceutically acceptable salt or solvate thereof.

5. The method according to claim 1, wherein the compound is sequirin C or a pharmaceutically acceptable salt thereof.

6. The method according to claim 1, wherein the compound is kazinol U or a pharmaceutically acceptable salt or solvate thereof.

7. The method according to claim 1, wherein the compound is kazinol U or a pharmaceutically acceptable salt thereof.

8. The method according to claim 1, wherein the disease state or condition mediated by the dopamine transporter is selected from: Parkinson's disease, bipolar disorder, clinical depression, attention deficit hyperactivity disorder (ADHD), narcolepsy, obstructive sleep apnea, night shift disorders, mood disorders, obesity, appetite suppression, cocaine addiction, methamphetamine addiction, antidepressant addiction, alcohol addiction and smoking addiction.

9. The method according to claim 1, wherein the pharmaceutical composition additionally comprises one or more further therapeutic agents specific for a disease state or condition being treated.

10. The method according to claim 1, wherein the pharmaceutical composition comprises agatharesinol, sequirin C, or kazinol U, or a pharmaceutically acceptable salt thereof, and wherein the disease state or condition mediated by the dopamine transporter is selected from: Parkinson's disease, bipolar disorder, clinical depression, attention deficit hyperactivity disorder (ADHD), narcolepsy, obstructive sleep apnea, night shift disorders, mood disorders, obesity, appetite suppression, cocaine addiction, methamphetamine addiction, antidepressant addiction, alcohol addiction and smoking addiction.

11. The method according to claim 1, wherein the pharmaceutical composition is formulated in a dosage form suitable for oral, parenteral, topical, intranasal, intrabronchial, sublingual, ophthalmic, otic, rectal, intra-vaginal, or transdermal administration to a subject.

12. The method according to claim 1, wherein the pharmaceutical composition additionally comprises one or more pharmaceutically acceptable excipients.

13. The method according to claim 2, wherein the disease state or condition mediated by the dopamine transporter is attention deficit hyperactivity disorder (ADHD).

14. The method according to claim 3, wherein the disease state or condition mediated by the dopamine transporter is attention deficit hyperactivity disorder (ADHD).

* * * * *